United States Patent [19]

Nylund

[11] Patent Number: 5,000,569

[45] Date of Patent: Mar. 19, 1991

[54] LIGHT REFLECTION DEFECT DETECTION APPARATUS AND METHOD USING PULSED LIGHT-EMITTING SEMICONDUCTOR DEVICES OF DIFFERENT WAVELENGTHS

[75] Inventor: Steven L. Nylund, Vancouver, Wash.

[73] Assignee: Lamb-Weston, Inc., Tri-Cities, Wash.

[21] Appl. No.: 291,237

[22] Filed: Dec. 28, 1988

[51] Int. Cl.$^5$ .................... G01N 21/27; G01N 21/89
[52] U.S. Cl. .................................. 356/237; 250/226; 356/402
[58] Field of Search ................ 356/237, 402; 250/226

[56] References Cited

U.S. PATENT DOCUMENTS

| | | | |
|---|---|---|---|
| 3,869,641 | 3/1975 | Goldberg | 315/135 |
| 3,887,836 | 6/1975 | Leete | 315/207 |
| 3,898,588 | 8/1975 | Skagerlund | 331/112 |
| 3,910,701 | 10/1975 | Henderson et al. | 356/39 |
| 3,993,899 | 11/1976 | Chapman | 250/227 |
| 4,276,983 | 7/1981 | Witmer | 209/587 |
| 4,520,702 | 6/1985 | Davis et al. | 83/71 |
| 4,558,786 | 12/1985 | Lane | 209/558 |
| 4,576,071 | 3/1986 | Rayment | 83/71 |
| 4,656,904 | 4/1987 | Rayment | 83/289 |

FOREIGN PATENT DOCUMENTS

0146299 6/1985 European Pat. Off.
2553309 6/1985 France.

*Primary Examiner*—Davis L. Willis
*Assistant Examiner*—Matthew W. Koren
*Attorney, Agent, or Firm*—Klarquist, Sparkman, Campbell, Leigh & Whinston

[57] ABSTRACT

A light-reflection defect detection apparatus and method for sensing the presence of food products or other articles and detecting defects therein is described using pulsed light-emitting semiconductor devices, such as light-emitting diodes (LEDs). The LEDs emit at least three different wavelengths of light including two of visible light (i.e., red and green light) and one of infrared light. Viewers each including photosensor, such as a photoelectric detector, are employed to sense the light reflected from the article and to produce sensor output signals which are sampled and stored before being transmitted to a digital computer for signal processing. The groups of LEDs are pulsed ON and OFF by a capacitor discharge pulse generator circuit which causes a substantially constant current to flow through the LEDs so that they emit light of uniform intensity. The defect detection apparatus and method is especially useful in detecting defects in elongated food products such as French-fry potato strips.

20 Claims, 7 Drawing Sheets

LIGHT REFLECTION DEFECT DETECTION APPARATUS AND METHOD USING PULSED LIGHT-EMITTING SEMICONDUCTOR DEVICES OF DIFFERENT WAVELENGTHS

BACKGROUND OF INVENTION

The present invention relates generally to defect detection apparatus and method for detecting defects in food products such as French-fry potato strips or other articles, including wood products, by light reflection and, in particular, to such defect detection apparatus and method employing pulsed light-emitting semiconductor devices for irradiating the products under investigation with light of different wavelengths and optical sensors with photoelectric detectors for detecting the light reflected from such products to determine whether they contain any defects.

It has been previously proposed in U.S. Pat. No. 4,576,071 of A. G. Rayment issued Mar. 18, 1986, for "Food Product Defect Sensor and Trimmer Apparatus" to provide a food product sensor and trimmer apparatus for detecting and removing defects from French-fry potato strips. The defect detector employs light sources in the form of incandescent light bulbs or halogen gas-filled lamps which generate "white" light of all visible frequencies and infrared light frequencies. Beam splitters in the form of hot mirrors and filters are used to separate such white light into beams of two different wavelengths including visible light and near-infrared (NIR) light. This prior defect detection apparatus had the disadvantage that such white light sources were ON substantially continuously and were of high power to provide sufficient light intensity which resulted in short useful lifetime and excessive heat buildup. It has been found that by using pulsed light-emitting semiconductor devices such as light-emitting diodes (LEDs), the short lifetime and excessive heat problems are solved, and sufficiently high intensity light is produced with a small fraction of the power dissipation previously required. As a result, pulsed LED light sources have a useful life at least ten times as long as the incandescent bulbs or the halogen gas light bulbs previously employed. In addition, the viewing apparatus is greatly simplified by elimination of the need for beam-splitting mirrors and filters since the desired color or wavelength of the light used to irradiate the product being tested for defects can be obtained directly from the LED. Thus, the correct wavelength light is obtained merely by selecting a light-emitting semiconductor device of the type whose light output is of the wavelength desired. This also enables the use of more than the two colors or wavelengths of light that are employed in the Rayment patent discussed above. Thus, by employing at least three different, separated wavelengths of light, the present defect detection apparatus is better able to detect defects and to distinguish between different types of defects.

Also of interest is U.S. Pat. No. 4,656,904 of A. G. Rayment issued Apr. 14, 1987, for "Food Product Cutter Apparatus" which discloses an improved cutter that may be employed in the defect sensor and trimmer apparatus of the above-discussed Rayment patent.

As disclosed in U.S. Pat. No. 4,520,702 of W. L. Davis, et al., issued June 4, 1985, for "Inspection and Cutting Apparatus," it has been proposed to provide an article inspection and cutting apparatus in which elongated articles such as French-fry potato strips are transmitted past scanning cameras to detect defects therein by sensing visible light reflected from such articles. The visible light emitted by a bank of incandescent lamps or fluorescent lamps apparently is white light containing all the wavelengths of visible light. Such apparatus does not provide light beams of different wavelengths in the manner of the above-described Rayment patent. In order to increase the intensity of illumination, the lamp bank is pulsed at a frequency synchronized to the scanning rate of the camera. The defect detection apparatus of the present invention is considerably faster and more accurate than that of Davis in that it does not employ a scanning camera. The scanning camera of Davis includes an electronically scanned linear diode array. However, the present invention employs a single diode photocell as a light sensor and employs light-emitting semiconductor devices, such as LEDs, as direct sources of different wavelength light to detect defects and to distinguish between different defects.

Also, unlike the above-discussed patents, in the present defect detection apparatus the LEDs are pulsed by a capacitor discharge circuit which provides a pulse of substantially constant current to cause light of substantially uniform intensity to be emitted therefrom.

It has been disclosed in U.S. Pat. No. 3,887,836 of Leete, issued June 3, 1975, for "Optical Driver Circuit," and U.S. Pat. No. 3,898,588 of Skagerlund, issued Aug. 5, 1975, for "Diode Laser Pumping" to provide light-emitting semiconductor devices such as LEDs which are pulsed ON by discharging a storage capacitor through such diodes. However, such LEDs are not employed in defect detection apparatus in the manner of the present invention.

SUMMARY OF INVENTION

It is, therefore, one object of the present invention to provide an improved defect detection apparatus and method capable of detecting defects in food products and other articles in a fast, accurate manner by using light reflection.

Another object of the invention is to provide such a defect detection apparatus and method in which optical sensors having photoelectric detectors sense light of different wavelengths reflected from the articles under examination to detect the presence of such articles and to determine whether such articles contain defects.

A further object of the invention is to provide such a defect detection apparatus in which a plurality of light-emitting semiconductor devices are employed to emit light of at least three different wavelengths including two of visible light and one of infrared in order to detect any defects in such articles and to more accurately distinguish between different types of defects.

Still another object of the invention is to provide such a defect detection apparatus in which light-emitting semiconductor devices are used as light sources in order to reduce power consumption and to reduce excessive heat generation, and are pulsed at high current for higher brightness and to increase the useful lifetime of such light sources.

An additional object of the invention is to provide such a defect detection apparatus in which the light-emitting semiconductor devices are pulsed in sequence to irradiate the articles with different wavelengths of light at different times in order to more clearly distinguish between the detected defects.

A still further object of the invention is to provide such a defect detection apparatus in which the light-emitting semiconductor devices are pulsed by capacitor discharge pulse generator circuits which cause a substantially constant current to flow through such devices and thereby generate high-intensity light of substantially uniform intensity for more accurate detection of defects.

A still additional object of the invention is to provide such a defect detection apparatus for detecting defects in food products such as French-fry potato strips in a fast, accurate manner to enable removal of such defects by cutting or by sorting out defective products.

DESCRIPTION OF DRAWINGS

Other objects and advantages of the present invention will be apparent from the following detailed description of a preferred embodiment thereof and from the attached drawings of which.

DESCRIPTION OF PREFERRED EMBODIMENT

Figure 1:
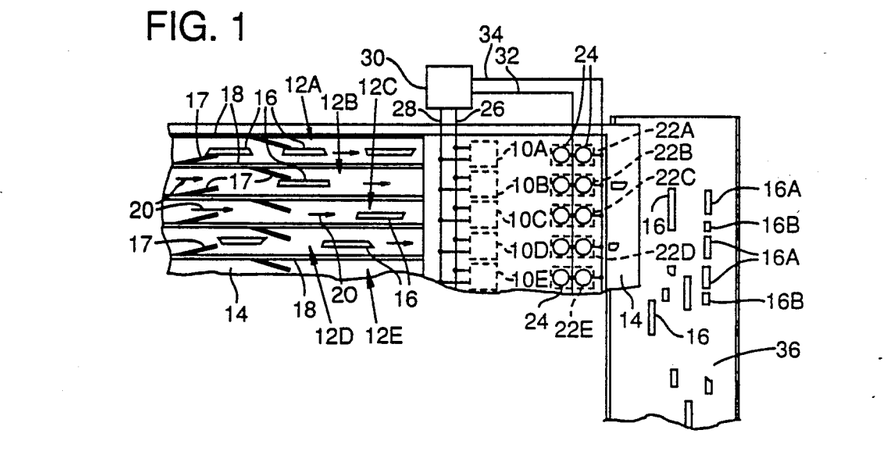
FIG. 1 is a plan view of a food product defect sensing and removal system which may employ the defect detector apparatus of the present invention, with parts removed for simplicity.

A food product defect sensor and trimmer system is shown in FIG. 1 employing several defect detection apparatus 10A, 10B, 10C, 10D, and 10E in accordance with the present invention, each positioned at the output of a different one of plurality of lanes 12A, 12B, 12C, 12D, and 12E provided on a feed conveyor belt system 14 for transmitting elongated food products 16 such as French-fry potato strips along such lanes. Each of the lanes 12 is separated from adjacent lanes by lane dividers 18 whose outlet ends terminate before the feed conveyor 14 passes under the defect detection apparatus 10A to 10E. The conveyor 14 conveys the potato strips 16 in such lanes from left to right in the direction of arrow 20 and such strips are aligned longitudinally by striking deflectors 17 which project partially into each lane from the opposite sides thereof. It should be noted that other conveyor and alignment systems can be employed including a system having a plurality of pairs of narrow conveyor belts, one pair for each lane, which can be selectively raised and lowered together with brushes for brushing any sideways strips from an upper to a lower belt so that they align the potato strips longitudinally at an alignment position without the use of deflectors 17 or lane dividers 19 before passing under detectors 10. After the aligned potato strips 16 pass beneath the defect detection apparatus 10A to 10E, they are transmitted through associated trimmer apparatus 22A to 22D, which may each contain a pair of piston-actuated cutters 24 for removing the defect in the manner shown in the above-discussed U.S. Pat. No. 4,656,904 of Rayment, et al.

The input and output signals of the defect detection apparatus 10A to 10E are transmitted through parallel bus lines 26 and 28 to a digital computer system 30 including a master computer and several slave computers, one for each lane. The slave computer controls the two cutters 24 in each trimmer apparatus 22A to 22E by output control signals on parallel output buses 32 and 34 to remove the defects of the French-fry potato strips 16. The cut potato strips 16A, along with the removed defects 16B and the uncut strips 16, fall from the end of the feed conveyor 14 onto a discharge conveyor 36 for discharge into packaging machines after the defects are removed, such as by a sorter screen (not shown), which allows such smaller defects to pass through such screen.

Figure 2:
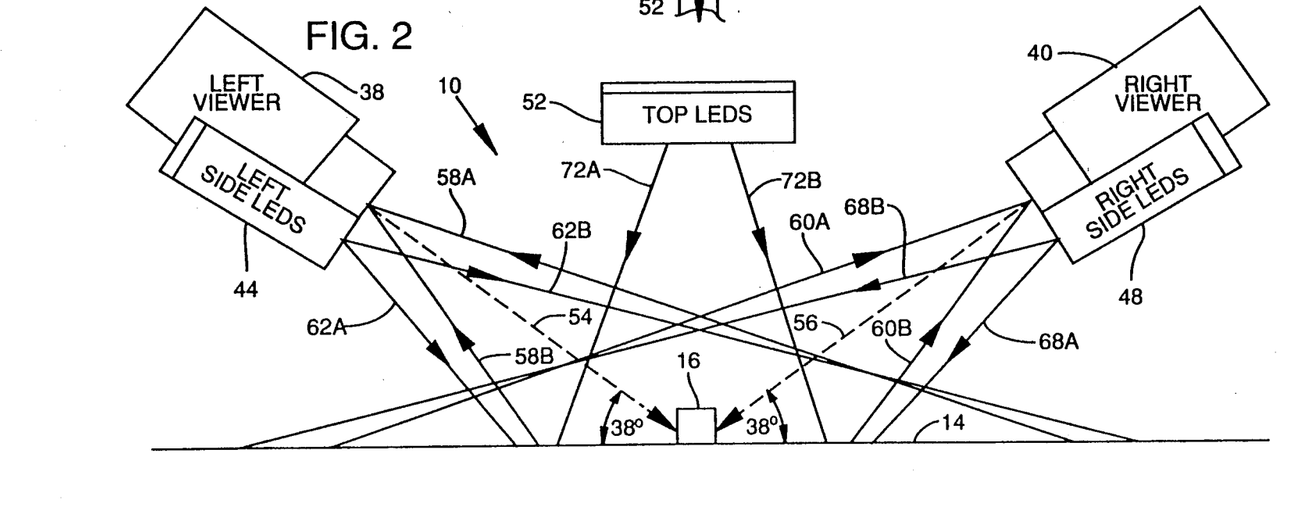
FIG. 2 is an elevation view of one end of a preferred embodiment of the defect detection apparatus of the present invention used for detecting defects in elongated food products such as French-fry potatoes.
Figure 3:
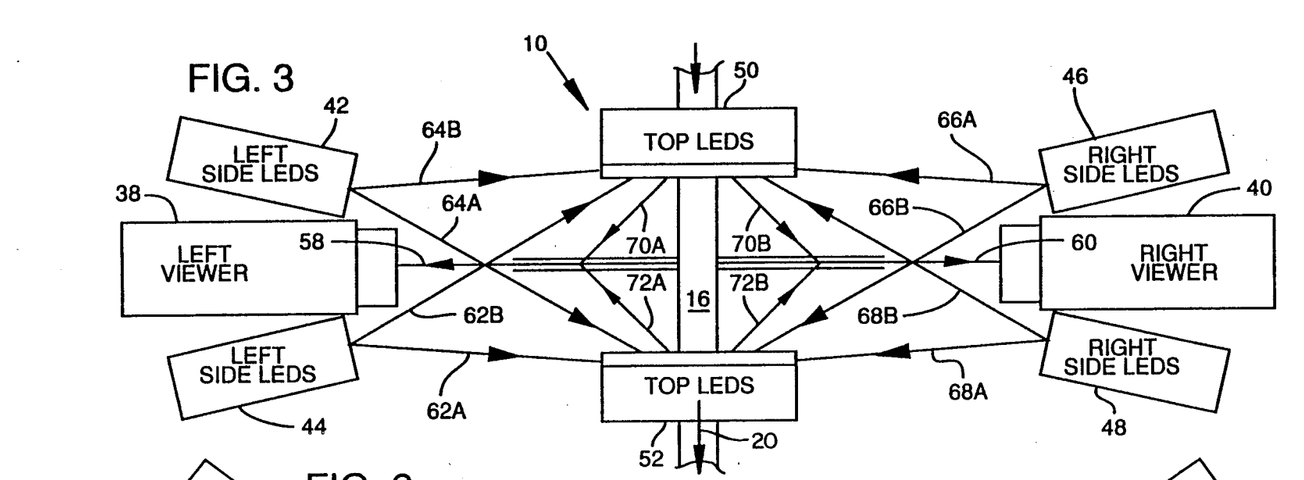
FIG. 3 is a top plan view of the apparatus of FIG. 2.

As shown in FIGS. 2 and 3, each defect detection apparatus 10 includes two optical sensors contained, respectively, within a left viewer 38 and a right viewer 40 on opposite sides of the French fry strip 16. The elements of a viewer are shown in greater detail in FIG. 5. In addition, such defect detection apparatus includes two left-side groups 42 and 44 of light-emitting semiconductor devices which may be LEDs for illumination of the left side of potato strip 16, two right-side groups 46 and 48 of right-side illumination LEDs, and two top groups 50 and 52 of top illumination LEDs. These groups of LEDs project light onto the top and the two sides of the French-fry strip 16 as it passes on conveyor 14 beneath the defect detection apparatus in the direction 20. The viewing field bounded in a vertical direction by rays 58A and 58B of the left viewer 38 is directed at the left side of the removing the defect in the manner shown in the abovediscussed U.S. Pat. No. 4,656,904 of Rayment, et al.

The input and output signals of the defect detection apparatus 10A to 10E are transmitted through parallel bus lines 26 and 28 to a digital computer system 30 including a master computer and several slave computers, one for each lane. The slave computer controls the two cutters 24 in each trimmer apparatus 22A to 22E by output control signals on parallel output buses 32 and 34 to remove the defects of the French-fry potato strips 16. The cut potato strips 16A, along with the removed defects 16B and the uncut strips 16, fall from the end of the feed conveyor 14 onto a discharge conveyor 36 for discharge into packaging machines after the defects are removed, such as by a sorter screen (not shown), which allows such smaller defects to pass through such screen.

Figure 5:
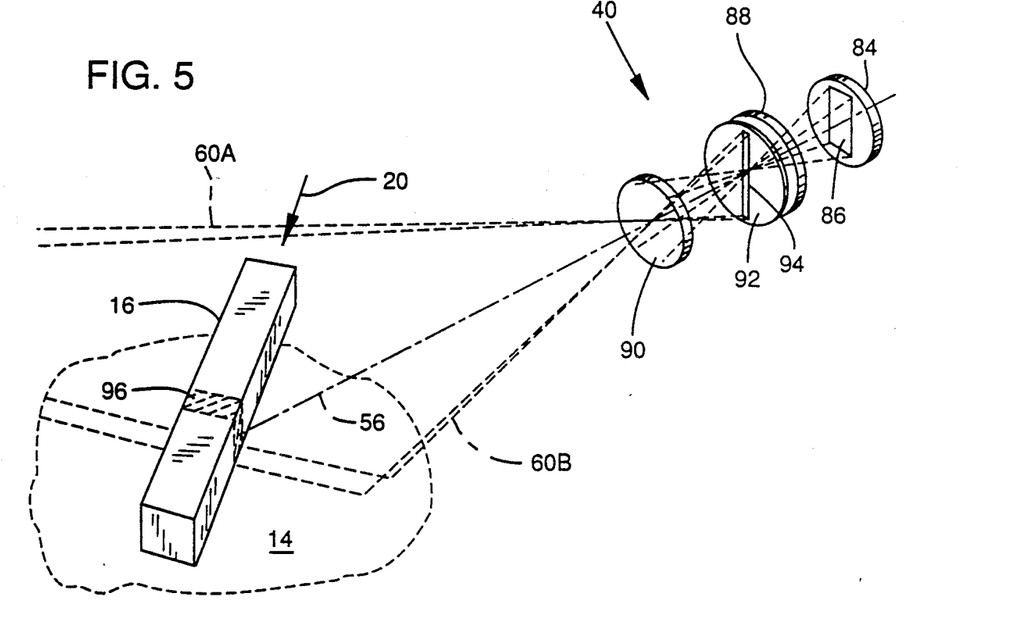
FIG. 5 is an enlarged oblique view of the elements in one of the viewers in the apparatus of FIGS. 2 and 3, including an optical sensor photocell which is employed to sense a food product.

As shown in FIGS. 2 and 3, each defect detection apparatus 10 includes two optical sensors contained, respectively, within a left viewer 38 and a right viewer 40 on opposite sides of the French fry strip 16. The elements of a viewer are shown in greater detail in FIG. 5. In addition, such defect detection apparatus includes two left-side groups 42 and 44 of light-emitting semiconductor devices which may be LEDs for illumination of the left side of potato strip 16, two right-side groups 46 and 48 of right-side illumination LEDs, and two top groups 50 and 52 of top illumination LEDs. These groups of LEDs project light onto the top and the two sides of the French-fry strip 16 as it passes on conveyor 14 beneath the defect detection apparatus in the direction 20. The viewing field bounded in a vertical direction by rays 58A and 58B of the left viewer 38 is directed at the left side of the French-fry strip 16 so that its central ray 54 makes an angle of approximately 38 degrees with the surface of the conveyor 14. However, the viewing field of such left viewer in the vertical plane indicated by rays 58A and 58B is sufficiently wide to cross the fry and cover the entire width of one lane. Similarly, the center ray 56 of the viewing field 60A and 60B of the right viewer 40 extends at an angle of approximately 38 degrees with respect to the conveyor belt 14. The viewing field of the right viewer 40 bounded vertically by rays 60A and 60B is wide enough to cross the fry and to cover the entire lane. However, as shown in the top view of FIG. 3, the viewing fields 58 and 60 of the viewers 38 and 40 are extremely narrow in a horizontal direction because they are limited by a slit aperture plate in the viewer as shown in FIG. 5 so that such beam intersects only a small section of the French-fry strip as it moves on the conveyor.

The projection fields 62A, 62B and 64A, 64B of the two left side groups of LEDs 44 and 42 are much wider horizontally than the viewing field of left viewer 40. The same is true of the projection fields 66A, 66B and 68A, 68B of the two right side groups of LEDs 46 and 48. Finally, the projection fields 70A, 70B and 72A, 72B of the two groups of top LEDs 50 and 52 also spread across the entire width of the lane to cross any French-fry in such lane, as shown in FIGS. 2 and 3. Thus, some of the light emitted by the LEDs is not reflected into the viewer but is wasted.

Figure 4:
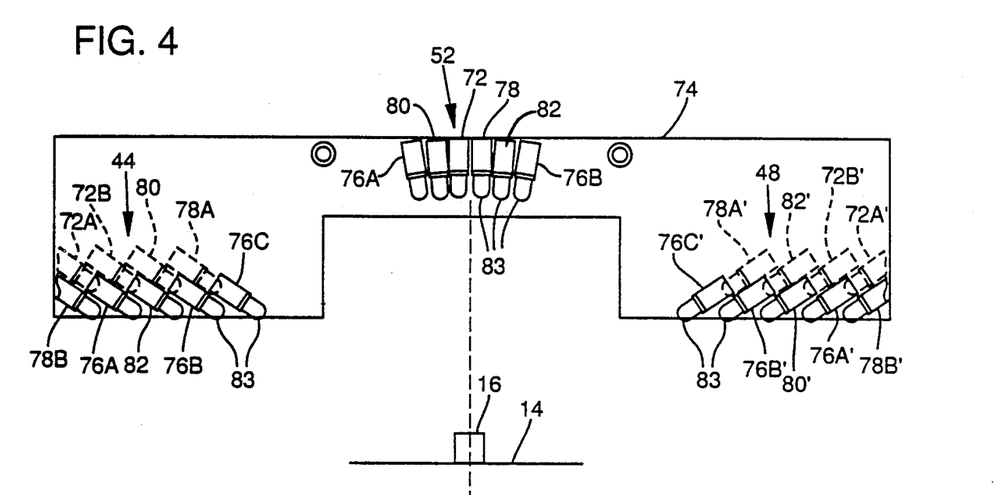
FIG. 4 is a front elevation view of an LED mounting board for the apparatus of FIGS. 2 and 3 showing the location on such board of the light-emitting semiconductor devices employed for irradiating the food product with light of different wavelengths.

As shown in FIG. 4, the groups of left-side LEDs 44, top LEDs 52, and right-side LEDs 48 are supported in three separate groups on a common support plate 74 which may be a printed circuit board having the connections of such LEDs to the pulser circuits provided thereon. A second support plate, not shown, supports the other three groups of LEDs 42, 46, and 50 in a similar manner.

The top group 52 of LEDs includes two green LEDs 76A and 76B at the opposite ends of such group, as well as a yellow LED 72 and a red LED 78 in the middle of the group, which all emit visible light of different wavelengths. It should be noted that the light emitted by the yellow LEDs with a wavelength of 570 nanometers is added to the light of the green LEDs to increase its intensity and to produce a combined bright green light having a wavelength of approximately 565 nanometers, since they are all pulsed ON at the same time. The red LED 78 emits light of a red color with a wavelength of 660 nanometers. In addition, an LED 80 emits invisible light in the near-infrared (NIR) range having a wavelength of 880 nanometers, while LED 82 emits NIR light of a wavelength of 940 nanometers.

The left side LED group 44 includes two yellow LEDs 72A and 72B; two red LEDs 78A and 78B; and three green LEDs 76A, 76B, and 76C. It also includes an NIR LED 80 of 880 nanometers wavelength and an NIR LED 82 which emits infrared light of 940 nanometers wavelength. The right-side group of LEDs 48 is similar to the left side in the spacing and positioning of the LEDs, so that the same numbers have been employed for corresponding LEDs except for adding a prime. However, it should be noted that the vertical positions of the LEDs 80' and 82' are reversed from that of LEDs 80 and 82 in group 44. Each of the LEDs includes a plastic lens 83 formed integral with its housing which focuses the light emitted therefrom to a beam angle of about 20 degrees.

As shown in FIG. 5, each of the viewers 38 and 40 includes a light sensor 84 having a photoelectric detector in the form of a single semiconductor diode photocell 82. The photocell may be a diode of silicon having a spectral response of about 450 nanometers to 1100 nanometers. The viewer also includes an upper lens 88 and a lower lens 90 which are separated by a slit aperture plate 92, such upper lens being positioned between the photocell and such aperture plate. The slit aperture plate 92 contains a narrow, rectangular slit 94 aligned vertically which limits the viewing field of the light-sensor 84 vertically to that bounded by the rays 60A and 60B and horizontally to the narrow width field which intersects the French-fry strip 16 in a narrow shaded area 96 about 1/16 inch wide. Thus, the viewing field receives light reflected from the shaded area 96 of the French-fry strip 16 and transmits such light through the slit 94 onto the photocell 96 for sensing the French-fry and detecting any defect in the shaded area 96 of such fry by producing an electrical output signal of corresponding amplitude. Since the French-fry moves longitudinally on conveyor 14 in the direction of arrow 20, the shaded area 96, where the viewing field 60 intersects such fry, scans along the entire length of the fry to detect any defects therein and also to measure the length of such fry in a manner hereinafter described.

Figure 6:
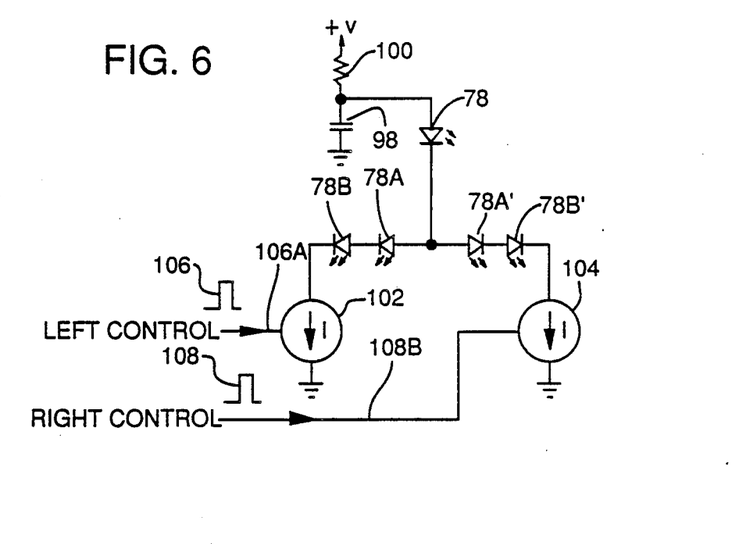
FIG. 6 is a schematic diagram of a pulse generator circuit employed to pulse one set of the light-emitting semiconductor devices ON to emit light of a predetermined wavelength in the apparatus of FIGS. 2 and 3.

A pulse generator circuit for pulsing ON and OFF one set of LEDs, which emit the same wavelength light, such as red light, is shown in FIG. 6. The circuit includes a charge storage capacitor 98 having its lower plate grounded and its upper plate connected through a current-limiting resistor 100 to a positive DC voltage source +V of, for example, +24 volts. Such current-limiting resistor may be of approximately 180 ohms resistance and such capacitor may be of approximately 1.0 microfarads capacitance. The top red LED 78 has its anode connected to the junction between resistor 100 and capacitor 98 and its cathode connected to the junction between two branches of series connected LEDs including the left side red LEDs 78A and 78B and the right side red LEDs 78A' and 78B'. Thus, the anodes of diodes 78A and 78A' are connected in common to the cathode of the diode 78, while the cathodes of diodes 78B and 78B' are connected to the upper terminals of two separate constant current sources 102 and 104, respectively, whose other terminals are grounded. Thus, current sources 102 and 104 are voltage controlled current sources which are switched ON at different times by rectangular trigger pulses 106 and 108, respectively, applied to the left control terminal 106A of current source 102 and to the right control terminal 108A of current source 104. Such trigger pulses 106 and 108 are produced at a time corresponding to a timing pulse generated by a shaft encoder (not shown) connected to the drive shaft of the supply conveyor 14, each timing pulse being generated at the start of each 1/16 inch segment of movement of the fry 16. These trigger pulses switch ON such current sources 102 and 104 at different times, as hereafter shown in FIG. 7A, and thereby discharge the capacitor through the LEDs connected to the conducting voltage source once for each increment of movement of the French-fry on the conveyor belt. Thus, a light reflection reading of each group of left and right LEDs is taken once for each 1/16 inch belt travel at a plurality of positions along the length of the French-fry, as hereafter described.

As a result of the operation of constant current sources 102 and 104, substantially constant currents flow through top LED 78 and the left LEDs 78A, 78B, or the right LEDs 78A' and 78B' to cause them to emit light of substantially uniform intensity during the entire width of the pulse produced by discharge of the capacitor 98 when such current sources are switched on by the control trigger pulse 106 or 108.

Figure 7A:
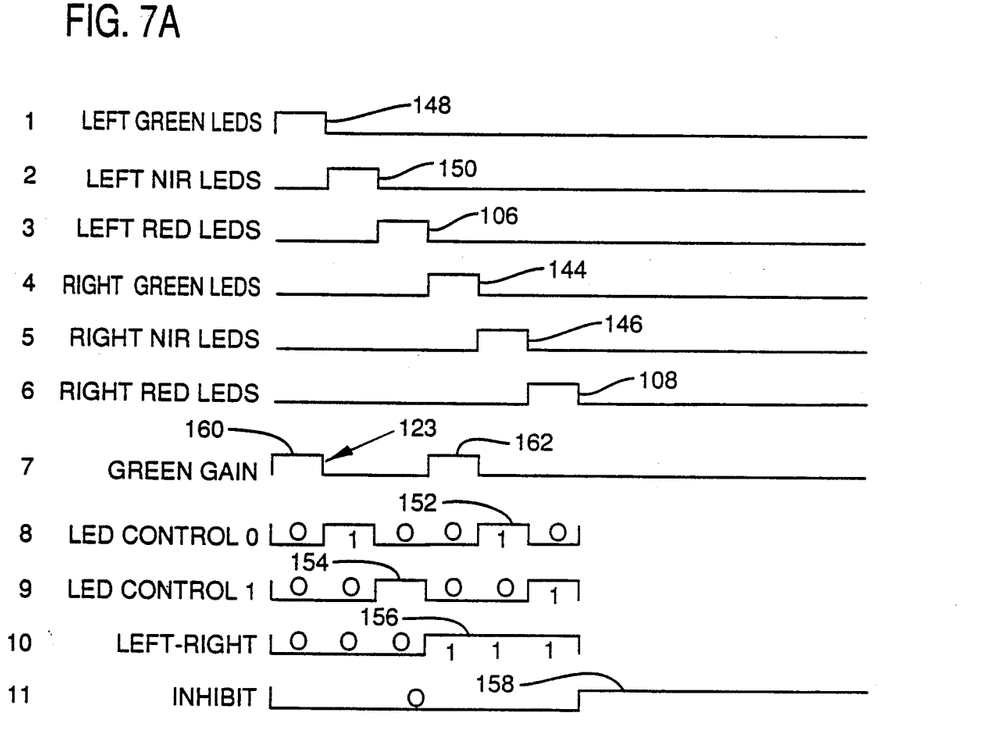
FIG. 7A is a diagram showing the timing pulses produced in the apparatus of FIGS. 2 and 3 for actuating the LEDs in sequence and for controlling the photosensor circuit.
Figure 8:
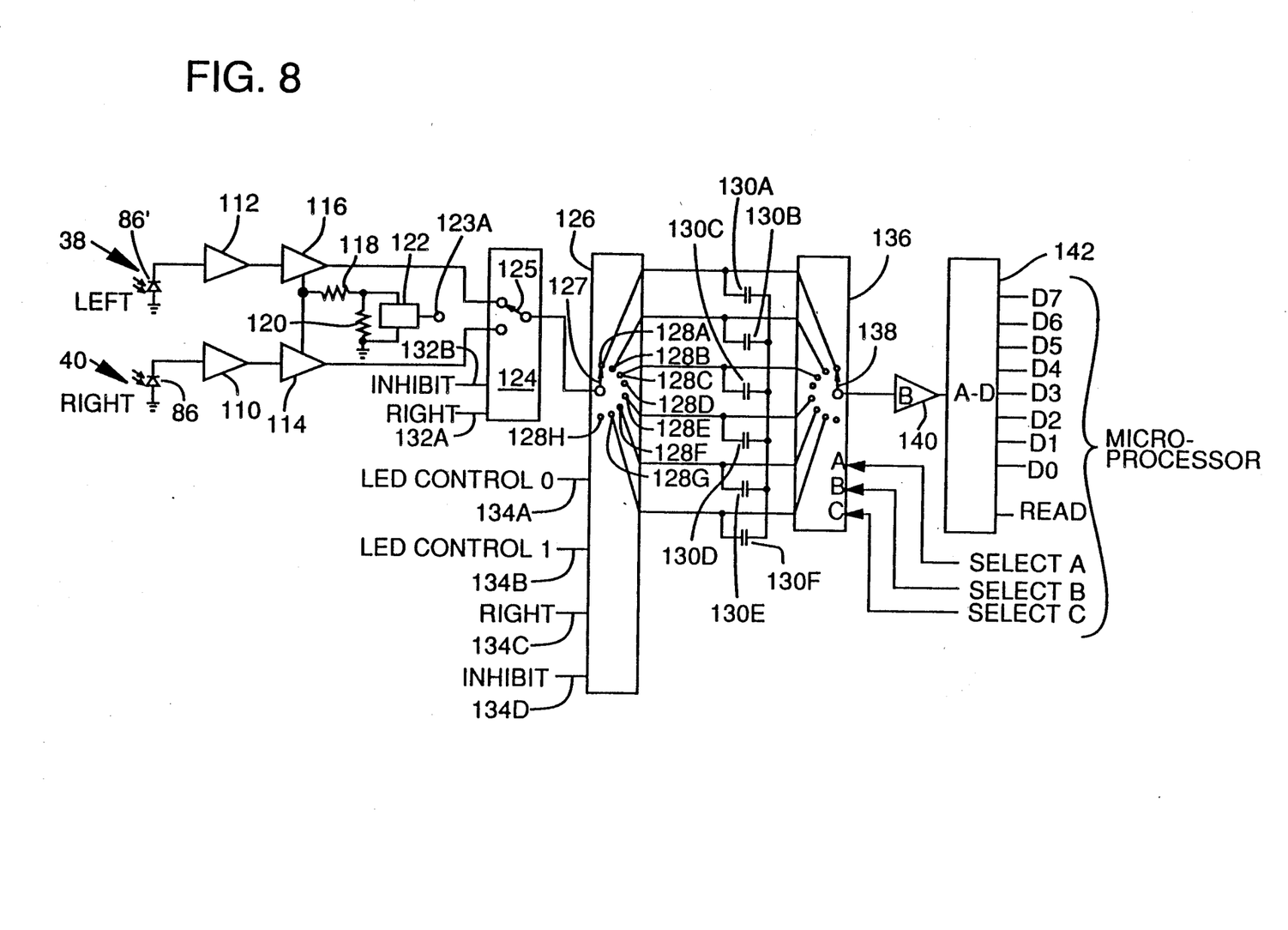
FIG. 8 is a schematic diagram of a photosensor circuit connected to the optical sensor photocells employed in the two viewers of FIGS. 2 and 3.

As shown in FIG. 8, the photocells 86 and 86' of the right and left viewers 40 and 38 are in the form of photoelectric diodes having their anodes grounded and their cathodes connected to the input of current to voltage converter amplifiers 110 and 112, respectively. The outputs of amplifiers 110 and 112 are connected to the inputs of gain controlled amplifiers 114 and 116, respectively. All four such amplifiers may be operational amplifiers of type LT 1057 integrated circuits. Amplifiers 114 and 116 have their reference voltage inputs connected in common to one end of a gain control resistor 118 of 2 kilohms whose opposite end is connected through a second gain control resistor 120 of 15 kilohms to ground. A switch 122 is connected in parallel with resistor 120 to short circuit such resistor when the switch is turned on and thereby increase the amplifier gain. Thus, the switch 122 is rendered conducting by a green gain signal 123 produced at a time corresponding to the detection of a green light reflection signal as shown in FIG. 7A. The green gain signal 123 is applied to control terminal 123A of switch 122 to reduce the gain control resistance thereby increasing the amplifier gain.

The outputs of amplifiers 114 and 116 are connected to two different inputs of a first analog multiplexer 124 which may be an integrated circuit of type CD4051B. The multiplexer 124 operates electronic switch 125 in a manner represented by rotation of a manual contact of switch 125 between these two different inputs to apply the analog output signals of the right photocell 86 and the left photocell 86' at different times to the input of a second analog multiplexer 126 which may be of the same type CD4051B integrated circuit. The second multiplexer has eight outputs 128A to 128H connected by the movable contact of its switch 127 to such input.

The first three outputs 128A, 128B, and 128C are connected to storage capacitors 130A, 130B, and 130C for storing the left green light signal, the left NIR light signal, and the left red light signal, respectively, produced by the left photocell 86'. The fourth output 128D is unconnected and represents a first OFF position of the input switch 127 of the second multiplexer. The fifth, sixth, and seventh positions 128E, 128F, and 128G of switch 127 are connected to capacitors 130D, 130E, and 130F for storing the right green light signal, the right NIR light signal, and the right red light signal, respectively, produced by the right side photocell 86. The eighth position 128H of switch 127 represents a second OFF position.

The storage capacitors 130A to 130F have one plate connected to the outputs of the switch 127 and have their other plate connected in common to ground so that each capacitor stores a different one of the output signals of the photocells 86 and 86' after amplification and sampling of such photocell signal voltage when the switches 125 and 127 are in the proper positions to transmit such signals to such capacitors. Thus, switch 127 and the storage capacitors 130 act as sample and hold circuits for sampling the output signals of the photocells at different times and holding or storing the sampled signal voltage. The multiplexers 124 and 126 are switched by control signals applied to control terminals 132A, 132B, and 134A, 134B, 134C, and 134D in a manner hereafter described relative to FIG. 7A.

A third analog multiplexer 136 of a type CD4051B integrated circuit is provided, including a switch 138 with its movable contact fixedly connected to an output terminal of such multiplexer and selectively connected to six input terminals, each connected to a different one of the six storage capacitors 130A to 130F. Thus, the output terminal of the multiplexer 136 is connected by switch 138 to a different one of the storage capacitors to transmit sensor output signals corresponding to the voltage stored on each such capacitor through a buffer amplifier 140 of a type AD712 integrated circuit to the input of an analog-to-digital converter 142 which may be a type AD7572 integrated circuit. The eight data outputs D0 to D7 of the converter 142 are connected to a microprocessor of a general purpose digital computer which compares the sensor signals corresponding to the intensity of the red, green, and NIR light reflected from the French-fry strip or other elongated article under investigation to sense the presence of such article, to measure its length, and to determine the nature of any defects in such article. The computer produces Select A, Select B, and Select C output control signals which are applied to the third multiplexer 136 to control the position of the movable contact of switch 138 in order to apply different sensor signals to the microprocessor of the CPU 30 after passing through the analog-to-digital converter 142.

Figure 7B:
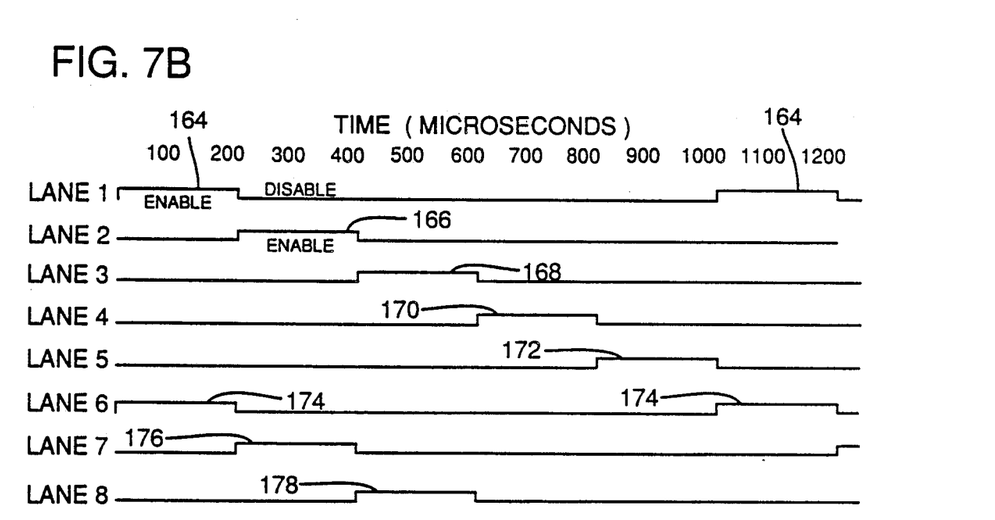
FIG. 7B shows system timing pulses for sequentially enabling the defect detection apparatus in each of eight lanes provided in the system of FIG. 1 to detect food products at different times.

FIG. 7A shows the timing of a sequence of six trigger signals for turning the different wavelength groups of LEDs ON and OFF sequentially and of five control pulses for the sensor circuits. The control pulses listed as signals 7 to 11 are applied to control terminal 123A of amplifiers 114, 116 and control terminals 132A, 132B, 134A, 134B, 134C, and 134D of multiplexers 124 and 126 to change the gain of such amplifiers and to cause the storage capacitors 130A to 130F of the photocell sensing circuit of FIG. 8 to sample and to store the voltages of the sensor signals. For example, the rectangular trigger signal 106 for the left red LEDs described in FIG. 6 is third in the sequence and turns on the left red LEDs and the top red LEDs for approximately 25 microseconds. Also, the sixth pulse is rectangular trigger signal 108 which turns on the right red LEDs and the top red LEDs for 25 microseconds a short time later. Thus, after pulse 106 terminates, the right green LEDs are turned on and off by trigger pulse 144 and then the right NIR LEDs are turned on and off by pulse 146, both for 25 microseconds. Following this, the right red LEDs are turned on by pulse 108. As shown in FIGS. 7A and 7B the trigger pulses each have an on/off duty cycle of much less than 50% so that each of the LEDs is pulsed off for a period many times greater than it is pulsed on.

At the start of the trigger pulse sequence, the left green LEDs are turned on first by rectangular trigger pulse 148 for approximately 25 microseconds. Thereafter, the right green LEDs are turned on by pulse 144 as the fourth pulse of the sequence. Also, the left NIR LEDs are turned on by the second pulse 150 for 25 microseconds before the right NIR LEDs are turned on by the fifth pulse 146. Thus, it can be seen that each of the six groups of LEDs are turned on at different times by the sequential trigger pulses 148, 150, 106, 144, 146, and 108 to prevent the sensor circuit of FIG. 8 from confusing the light of different groups reflected from the French-fry or other article. This will allow the production of a sensor output signal at the output of multiplexer 136 in FIG. 8 of the proper voltage which corresponds to the reflected light intensity of one of the six groups of LEDs at a time.

The control pulse signals include an "LED Control 0" signal 152 applied to the control terminals 134A and an "LED Control 1" signal 154 applied to control terminal 134B of multiplexer 126. A "Left-Right" control signal 156 is applied to terminal 132A of multiplexer 124 and to terminal 134C of multiplexer 126. An "Inhibit" signal 158 is applied to termial 132B of multiplexer 124 and to terminal 134C of multiplexer 126. The control signals 152, 154, 156, and 158 are rectangular pulse signals which are arranged in a 4-bit binary code as shown in FIG. 7A to operate the multiplexers 124 and 126 so that the storage capacitors 130A to 130F are connected to the outputs of photocells sequentially in the proper order to store the desired LED group signal as indicated in the following table:

| Control Signal | 130A Left Green | 130B Left NIR | 130C Left Red | 130D Right Green | 130E Right NIR | 130F Right Red |
| --- | --- | --- | --- | --- | --- | --- |
| LED Control 0 | 0 | 1 | 0 | 0 | 1 | 0 |
| LED Control 1 | 0 | 0 | 1 | 0 | 0 | 1 |
| Right-Left | 0 | 0 | 0 | 1 | 1 | 1 |
| Inhibit | 0 | 0 | 0 | 0 | 0 | 0 |

This causes the proper voltage to be stored on the storage capacitors 130A to 130F at the end of LED pulses 148, 150, 106, 144, 146, and 108 and to cause such stored voltages to be transmitted as output signals from multiplexer 136 to the microprocessor.

Also, FIG. 7A shows that the "Green Gain" signal 123 applied to switch 122 of the amplifiers 114 and 116 of FIG. 8 closes such switch to short circuit resistor 120 with positive pulses 160 and 162 only when the green LEDs are pulsed ON by trigger pulses 148 and 144. Thus, the gain of the amplifiers 114 and 116 is only increased by pulses 160 and 162 when sensing green light because such green light is of lower intensity.

As shown in FIG. 7B, positive enabling pulses 164, 166, 168, 170, 172, 174, 176, and 180 are applied sequentially to each of the eight defect detection apparatus 10A, 10B, 10C, 10D, etc., in the eight different lanes of the conveyor to enable the LEDs of the corresponding defect detection apparatus to be turned on only during such enabling pulse. This prevents light reflections from an article in one lane to detector apparatus in adjacent lanes which otherwise could cause erroneous signal readings in the photosensors.

Figure 9:
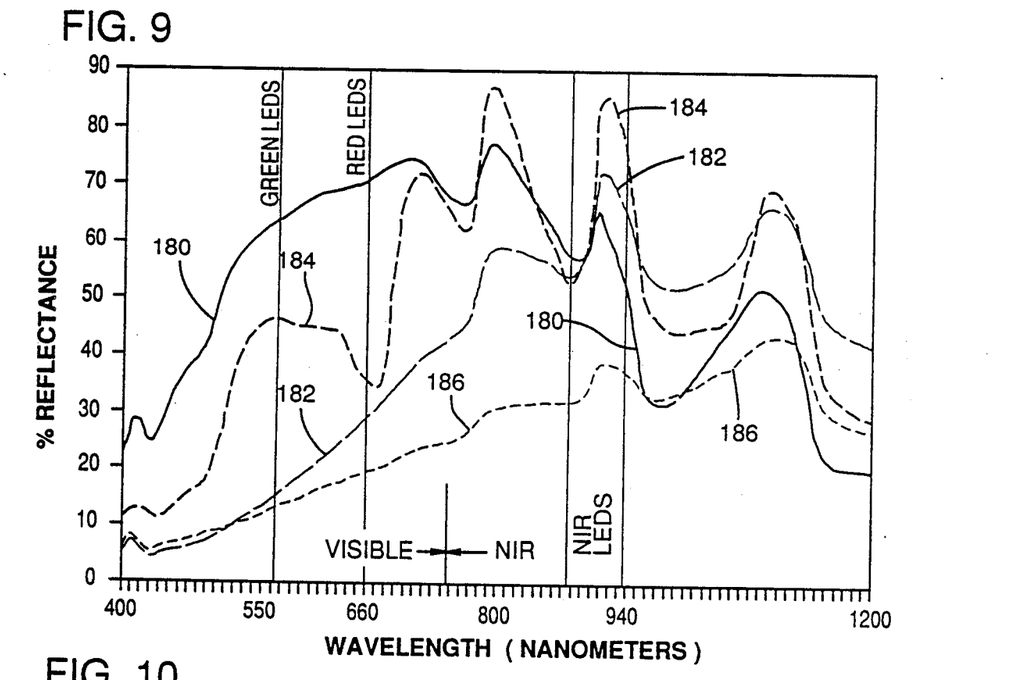
FIG. 9 is a diagram showing curves of light reflectance from French-fry potato strips at different light wavelengths and under different surface conditions including defects.

As shown in the graph of FIG. 9, the amount of light reflectance of different wavelengths from the French-fry potato strip varies depending upon whether the potato portion being irradiated is a good whitecolored potato portion whose reflectance is as shown in curve 180, or is a defect such as a brown potato skin portion of curve 182, a green potato defect of curve 184, and a rotten defect of curve 186. At the green light wavelength of 565 nanometers produced by the green and yellow LEDs, approximately 63 percent of the light is reflected from the good white potato portions as indicated on curve 180. However, the brown skin portions only reflect approximately 15 percent of such green light at this wavelength as indicated on curve 182. Also, approximately 46 percent of the green wavelength light is reflected from the green defect portions of the potato as indicated on curve 184. The rotten defect portions of the potato reflect only approximately 12 percent at a wavelength of 565 nanometers as indicated by curve 186.

At the red light wavelength of 660 nanometers which is emitted by the red LEDs, the good white potato portions reflect about 70 percent of the light as indicated on curve 180. The brown skin portions reflect approximately 27.5 percent of such red light per curve 182, while the green defect portions reflect about 35 percent of the red light on curve 184 at such wavelength. The rotten portions of the potato reflect only 18 percent of the red wavelength light, according to curve 186. However, for NIR light of 880 and 940 nanometers wavelength, the reflectance of the good white potato portion 180, the brown skin defects 182, and the green defects 184 are all of substantially the same reflectance. For example, at an NIR wavelength of 880 nanometers, white potato reflectance is 52 percent on curve 180, brown skin reflectance is 53 percent on curve 182, and green defect reflectance is 57 percent on curve 184. Therefore, the NIR light reflectance is used to detect the presence of a potato strip and to measure its length. It is easier to differentiate the green defects 184 from the white potato portions 180 at the red light wavelength because they differ by about 35 percent. Also, it is easier to detect the brown skin portions 182 and the rotten black portions 186 from the good white potato 180 at the green light wavelength because they differ by about 48 percent. Thus, at least three different wavelengths of light are necessary to detect all defects and to distinguish between certain types of defects.

As discussed above, NIR light is employed to detect the presence of the French-fry potato strips and to measure the length of such strips, not the presence of defects. However, the ratio of the green light reflectance divided by NIR light reflectance and the ratio of red light reflectance divided by NIR light reflectances are determined by the computer to improve the ability to distinguish between certain defects, regardless of the size of the potato strip. In the example given in FIG. 9, the NIR light of 880 nanometers is reflected from good white potato at 57 percent and from rotten defects 186 at a level of 32 percent, while it is reflected from brown skin 182 at 53 percent and from green potato defect at 52 percent.

The green light divided by NIR reflectance ratios are:

| | | |
|---|---|---|
| 46/52 = 0.88 | green potato defect | |
| 63/57 = 1.1 | white potato | |
| 15/53 = 0.28 | brown skin defect | |
| 12/32 = 0.37 | rotten defects | |

However, the red light divided by the NIR reflectance ratios are:

| | | |
|---|---|---|
| 35/52 = 0.67 | green potato defect | |
| 70/57 = 1.23 | white potato | |
| 27.5/53 = 0.52 | brown skin defect | |
| 18/32 = 0.56 | rotten defect | |

Thus, the red light/NIR ratios provide the best detection of the green potato defect from the white potato. However, the green light/NIR ratio provides the best detection of brown skin and rotten defects, as well as the other nongreen defects from good white potato and clear distinction from the green potato defect.

Figure 10:
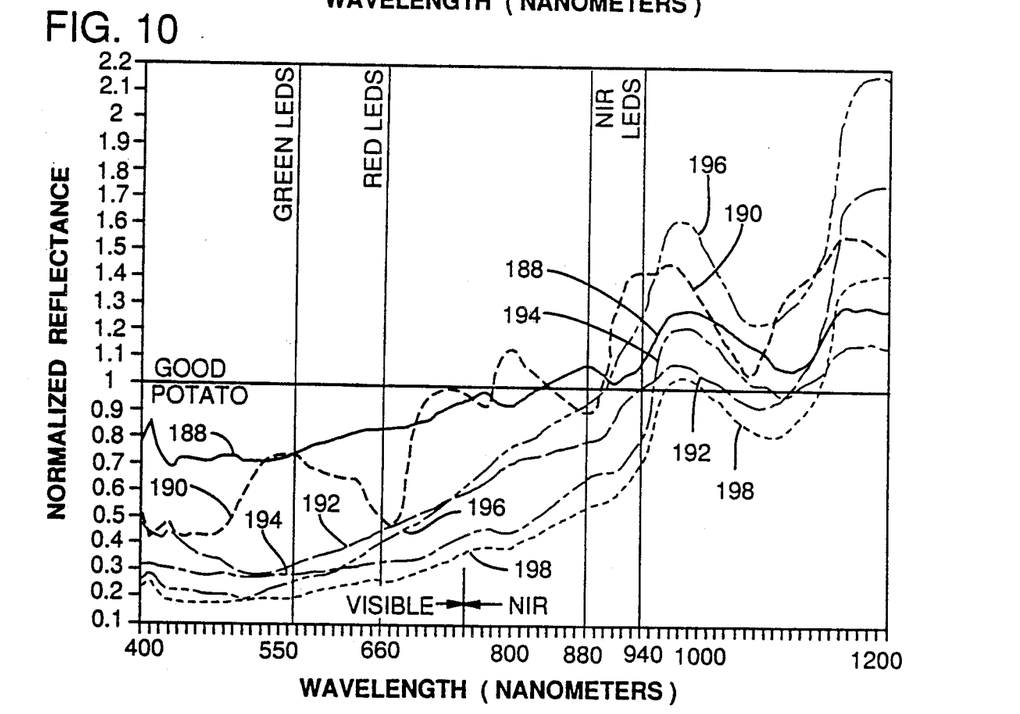
FIG. 10 is a schematic diagram showing the normalized light reflectance from various defects on the potato divided by the signal produced by light reflection from a good potato.

The light reflectance curves are "normalized" by dividing the defect reflectances by that of the good white potato in curve 180 to provide in FIG. 10 curves of several defects including heat necrosis 188, green defect 190, hollow heart 192, scab 194, skin 196, and rot 198. From these curves, it is easy to see that green defects 190 are the only defects that have a lower normalized reflectance at the red wavelength than at the green wavelength. This makes it possible to distinguish green defects from other defects.

It should be noted that at the NIR wavelength of 880 nanometers, the defects have a normalized reflectance predominantly less than 1.0, while at an NIR of 940 nanometers, such defects have a normalized reflectance mostly greater than 1.0. This is the reason why both NIR wavelengths are used to detect the presence of the potato, since together their average normalized reflectance is approximately 1.0. Thus, by employing two separate visible light wavelengths, together with two NIR wavelengths, the defect detection apparatus of the present invention is able to more accurately sense potato strips, to measure their length, to detect defects, and to distinguish between different defects.

Figure 11:
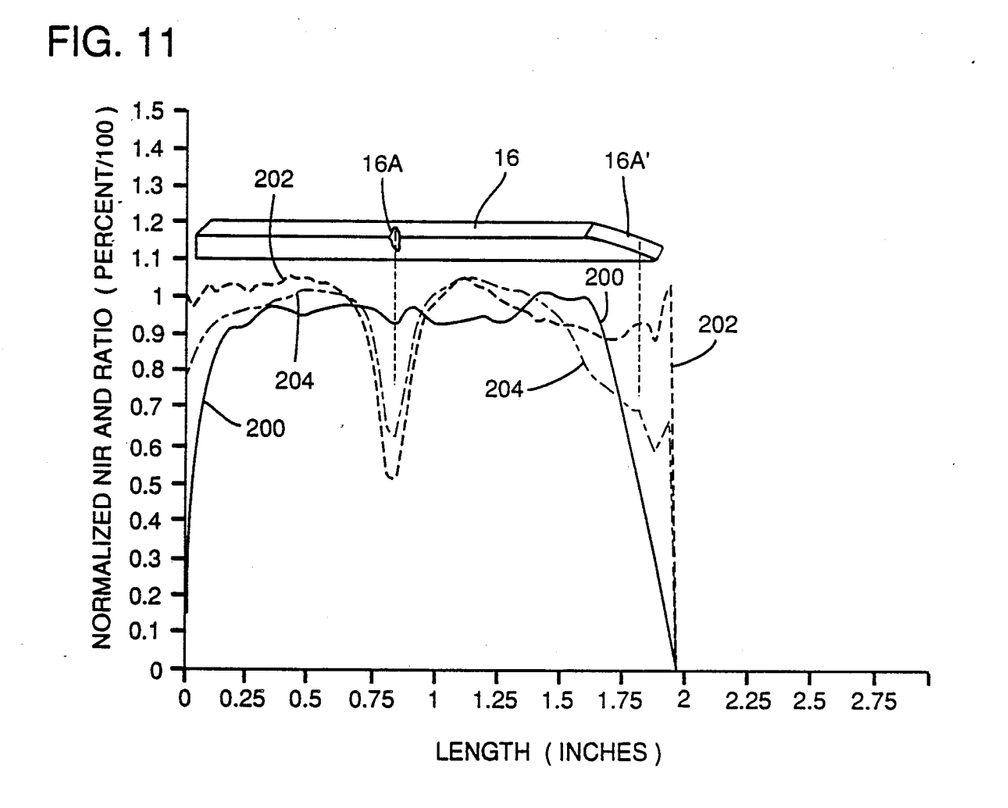
FIG. 11 is a diagram of curves showing the percentage of light reflectance of different wavelengths from a French-fry potato strip at different spaced positions along such potato strip including two different types of defects.

FIG. 11 shows the results of defect testing by the percentage changes in the output signals of the photosensors as they scan along the French-fry potato strip 16 from its left end to its right end for a potato strip which is approximately two inches long and tapered at its right end where a green area defect 16B is present. Thus, the output signal for NIR light is a curve 200 which is substantially constant along the entire length of the potato strip, including a middle portion having a small defect 16A, but which decreases from 100 percent at a position of 1.65 inch to zero percent at 2.0 inches because of the reduction in vertical thickness at the tapered right end of the fry. However, the output signal for a green ratio curve 202, which is the ratio of the green light signal divided by the NIR signal, reduces dramatically at the small defect 16A from a 100 percent signal at a position of about 0.65 inch to a minimum of about 52 percent at 0.80 inch and then returns to a value of 100 percent at about 1.00 inch where it stays until the end of the fry at 2.0 inches. The same small defect 16A is detected by the red ratio curve 204 for the red wavelength output signal divided by the NIR signal output. However, the red ratio curve 204 also indicates a dramatic reduction of amplitude in the neighborhood of the green defect area 16A' where it reduces from 100 percent at about 1.4 inches to 90 percent at approximately 1.55 inch and thereafter to a value of 70 percent at approximately 1.80 inch to a minimum of 60 percent at a value of about 1.85 inch. Thus, the red ratio curve 204 is most suitable for detecting the green area defect 16A', while the green ratio curve 202 is most suitable for indicating the other defect 16A such as a skin defect, rot, scab, hollow heart, or heat necrosis. By employing the red and green ratios as indicated, the defects are detected and identified, regardless of the size of the potato strip. For example, if the reduction of the red ratio 204 is greater than the reduction of the green ratio 202, such as at 16A', we know that the defect is a green-area defect. However, if the reduction of the green ratio is greater than the reduction of the red ratio, such as at 16A, we know that it is another defect such as a skin defect.

It will be obvious to those having ordinary skill in the art that many changes may be made in the above-described preferred embodiment of the present invention. Therefore, the scope of the present invention should be determined by the following claims.

I claim:

1. Defect detection apparatus for detecting defects in articles, comprising:

optical sensor means for sensing articles and for scanning the articles to detect any defects therein;

a plurality of light-emitting semiconductor devices including first devices which emit light of a first wavelength and second devices which emit light of a second wavelength different from said first wavelength, at least one of said wavelengths being visible light;

pulser means for applying electrical pulses to control said semiconductor devices to actuate said first and second devices on and off, said pulses having an on/off duty cycle of much less than 50% so that each of said devices is pulsed off for a period many times greater than it is pulsed on;

illumination means for directing the emitted light of said first and second wavelengths at said articles in projection fields wider than the sensed article to cause said light to be reflected from the exposed three dimensional surface of the sensed article and from any defects on said surface; and viewer means for receiving said reflected light and directing it to said optical sensor means which measure the amount of reflected light to detect defects in said articles.

2. Apparatus in accordance with claim 1 in which the first and second wavelengths are in the visible light and infrared light wavelength range.

3. Apparatus in accordance with claim 1 in which the semiconductor devices include third devices which emit light of a third wavelength different from said first and second wavelengths.

4. Apparatus in accordance with claim 3 in which the first wavelength is infrared light and the second and third wavelengths are visible light.

5. Apparatus in accordance with claim 1 in which the semiconductor devices are light-emitting diodes.

6. Apparatus in accordance with claim 1 in which the pulser means includes a plurality of capacitor discharge pulse generator circuits connected to different ones of said first and second devices.

7. Apparatus in accordance with claim 6 in which the capacitor discharge pulse generator circuits include constant current means for applying a current output pulse of substantially constant current to said devices.

8. Apparatus in accordance with claim 1 in which the optical sensor means includes photoelectric detectors which produce electrical output signals when they receive said reflected light, the amplitude of said output signals corresponding to the intensity of the received reflected light and indicating whether a defect is present as well as identifying the type of defect.

9. Apparatus in accordance with claim 1 which also includes conveyor means for conveying said articles past said viewer means to cause said articles to be scanned by said optical sensor means.

10. Apparatus in accordance with claim 1 in which the articles are food products.

11. Apparatus in accordance with claim 10 in which the food products are French-fry potato strips and the viewer means illuminates the top and two opposite sides of said strips with light of said first and second wavelengths and with light of a third wavelength, two of such wavelengths being visible light and the third wavelength being infrared light.

12. A method of detecting defects in articles, comprising the steps of:
   emitting light of at least three different wavelengths, including visible light, each wavelength being emitted from different light-emitting devices;
   pulsing said devices on and off with electrical pulses having an on/off duty cycle of much less than 50% so that each of said devices is pulsed off for a period many times greater than it is pulsed on;
   directing light beams of said light pulses at an article to be sensed in projection fields wider than the sensed article to illuminate the exposed threedimensional surfaces of said article substantially uniformly and to reflect said light pulses from said surfaces and from any defects on said surfaces;
   detecting reflected light from said article corresponding to said light beams by photoelectric detector means to produce electrical sensing signals of different amplitudes; and
   processing said sensing signals to determine the presence of an article, to determine whether it contains a defect from the reflected visible light, and to identify any defect.

13. A method in accordance with claim 12 in which the sensed article is scanned by said light beams over substantially its entire exposed surfaces to detect and defects therein.

14. A method in accordance with claim 13 in which said devices are light-emitting diodes.

15. A method in accordance with claim 12 in which two of the wavelengths are visible light and the third wavelength is infrared light.

16. A method in accordance with claim 12 in which groups of light-emitting devices are pulsed on sequentially so that light pulses of the same wavelength are emitted at a given time.

17. A method in accordance with claim 16 in which the pulsing step includes discharging a storage capacitor through the devices and controlling the discharge current to maintain a substantially constant current through such devices.

18. A method in accordance with claim 12 in which the article under investigation is a food product.

19. A method in accordance with claim 17 in which the food product is a French-fry potato strip.

20. Defect detection apparatus for detecting defects in articles, comprising:
   optical sensor means for sensing articles and for scanning the articles to detect any defects therein;
   a plurality of light-emitting semiconductor devices including first devices which emit light of a first wavelength and second devices which emit light of a second wavelength different from said first wavelength, at least one of said wavelengths being visible light;
   pulser means for applying electrical pulses to said semiconductor devices to actuate said first and second devices at different times, each of said devices being turned on for much less time than it is turned off during an on/off cycle and the pulses being of substantially constant current;
   illumination means for directing the emitted light of said first and second wavelengths at said articles in projection fields wider than the sensed article to cause said light to be reflected from the exposed three dimensional surface of the sensed article and from any defects on said surface; and
   viewer means for receiving said reflected light and directing it to said optical sensor means which measure the amount of reflected light to detect defects in said articles.

* * * * *

UNITED STATES PATENT AND TRADEMARK OFFICE
CERTIFICATE OF CORRECTION

PATENT NO. : 5,000,569

DATED : March 19, 1991

INVENTOR(S) : Steven L. Nyland

It is certified that error appears in the above-identified patent and that said Letters Patent is hereby corrected as shown below:

On the title page, items:

[56] References Cited, FOREIGN PATENT DOCUMENTS "2553309 6/1985 France" should be --2553309 4/1985 France--;

[57] ABSTRACT, line 8, after "including" insert --a--;

Column 4, line 48 through column 5, line 12, delete in its entirety (duplicate printing);

Column 12, line 58, claim 1, after "articles" insert --and to determine the position of said defects on the articles for removal of the defects--;

Column 13, lines 42 and 43, claim 12, "threedimensional" should be --three-dimensional--;

Column 14, line 1, claim 12, after "and to" insert --determine the position of the defect on the article for removal of said defect and comparing said sensing signals to distinguish between different types of defects--;

Column 14, line 2, claim 12, delete "identify any defect";

Column 14, line 5, claim 13, delete "and" and insert --any--;

UNITED STATES PATENT AND TRADEMARK OFFICE
CERTIFICATE OF CORRECTION

PATENT NO. : 5,000,569

DATED : March 19, 1991

INVENTOR(S) : Steven L. Nyland

It is certified that error appears in the above-identified patent and that said Letters Patent is hereby corrected as shown below:

Column 14, line 50, claim 20, after "articles" insert --and to determine the position of the defect on the article for removal of the defect--.

Signed and Sealed this

Twenty-second Day of February, 1994

Attest:

BRUCE LEHMAN

Attesting Officer     Commissioner of Patents and Trademarks